United States Patent [19]

Dolan

[11] 4,237,721
[45] * Dec. 9, 1980

[54] APPARATUS AND METHOD FOR DETECTING SUBSTANCES AND FOR REGULATING CURRENT

[75] Inventor: James P. Dolan, Seattle, Wash.

[73] Assignee: ADS Systems, Inc., Seattle, Wash.

[*] Notice: The portion of the term of this patent subsequent to Dec. 12, 1995, has been disclaimed.

[21] Appl. No.: 968,026

[22] Filed: Dec. 11, 1978

Related U.S. Application Data

[63] Continuation-in-part of Ser. No. 841,802, Oct. 13, 1977, Pat. No. 4,129,030.

[51] Int. Cl.³ .............................................. G01N 27/04
[52] U.S. Cl. ...................................................... 73/23
[58] Field of Search ................. 73/23, 27 R; 340/632, 340/634; 23/232 E; 422/98; 338/13, 27, 34, 35

[56] References Cited

U.S. PATENT DOCUMENTS

| | | | |
|---|---|---|---|
| 3,045,198 | 7/1962 | Dolan et al. | 338/13 |
| 3,247,478 | 4/1966 | Craig | 338/35 |
| 3,507,145 | 4/1970 | Loh | 73/27 R |
| 3,879,985 | 4/1975 | Maslen | 73/27 R |

Primary Examiner—Stephen A. Kreitman
Attorney, Agent, or Firm—Seed, Berry, Vernon & Baynham

[57] ABSTRACT

An apparatus and method for sensing liquids, vapors and gases, which includes a conventional detection device operated in its non-linear region so that it is sensitive not only to substances having a Van der Waals' constant of greater than 9, but it is also sensitive to substances having a Van der Waals' constant of 9 or less. The device is driven by a constant current source, and a change in the level of the voltage across the detection device occurs upon exposure of the device to the substance being sensed. This voltage change is then detected to indicate the presence of the sensed substance. The relatively small voltage change associated with the detection device may be easily sensed by placing the detection device in a balanced bridge circuit. Further, the bridge circuit enables easy, accurate normalization of the apparatus in a reference environment. The non-linear characteristics of the detector allow it to be employed as a regulator for supplying a constant current to a power consuming device.

12 Claims, 5 Drawing Figures

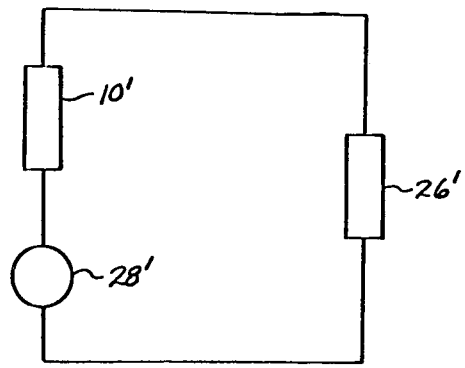
Fig. 3
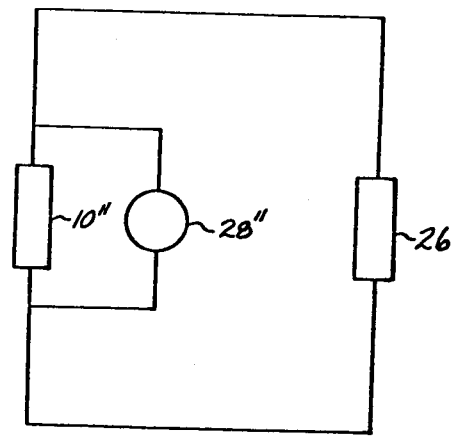
Fig. 4
| VAN DER WAALS' "a" CONSTANT | GAS | CURRENT CHANGE BETWEEN TERMINALS 14, 16 |
|---|---|---|
| 2.25 | METHANE | 310 MICROAMPERES |
| 3.59 | CARBON DIOXIDE | 405 MICROAMPERES |
| 4.39 | ACETYLENE | 625 MICROAMPERES |
| 5.48 | ETHANE | 725 MICROAMPERES |
| 8.66 | PROPANE | 1850 MICROAMPERES |
Fig. 5

APPARATUS AND METHOD FOR DETECTING SUBSTANCES AND FOR REGULATING CURRENT

CROSS REFERENCE TO RELATED APPLICATIONS

This is a continuation-in-part of application Ser. No. 841,802, filed Oct. 13, 1977, now U.S. Pat. No. 4,129,030.

BACKGROUND OF THE INVENTION

1. Field of the Invention

The present invention relates to an apparatus and method for sensing liquids, vapors and gases and to a current regulating device and, more particularly, to a method and apparatus for electrically sensing liquids, vapors and gases having virtually any Van der Waals' constant and to a nonlinear device for maintaining a relatively constant current through the device responsive to variations in voltage across the device.

2. Description of the Prior Art

It is an increasingly important task in any industrial society to detect the presence of the liquid, vaporous and gaseous substances. For example, detection may be of consequence since the substance may be intrinsically hazardous due to its explosive, flammable, toxic or noxious character. Obviously, detection is doubly important when such substances enter confined areas where they are unwanted, such as living spaces, mines, bilges, storage tanks, trailers aircraft and the like.

Detection may also be important where, although the substance is not particularly perilous in itself, its presence is an indication of some undesirable condition. For example, a hazardous fire may be detected by its early products of combustion which are not as hazardous as the fire itself. Similarly, the presence of a particular substance in the environment surrounding the detecting apparatus may indicate a leak in a supposedly tight system.

One detection devices used in the present invention is disclosed in U.S. Pat. No. 3,045,198, issued July 17, 1962, to Dolan et al. In its basic form, the detection device disclosed in the Dolan et al patent includes a layer of resilient material which is secured to a rigid base member. The active element, a stratum discrete, electrically conductive, adsorbent particles, adheres to the layer of resilient material, which serves to individually anchor each particle. A pair of spaced apart electrodes are in electrical contact with the stratum of conductive, adsorbent particles. Under reference conditions, as upon exposure to pure atmospheric air, the detection device will normalize and develop a characteristic resistance between the electrodes which is a function of the resistance of the stratum of conductive, adsorbent particles located between the electrodes. However, when the detection device is exposed to the liquid, vapor or gas being sensed, it is found that its resistance changes, usually by increasing.

What is believed to occur is that, in accordance with known principles, minute quantities of the substance being sensed are adsorbed onto the surface of each adsorbent particle, thereby forming a uniform, monomolecular layer which coats the surface thereof. The force of adsorption, known as the Van der Waals' adsorption force, is so great that the layer of adsorbed substance will actually interpose itself between adjacent adsorbent particles which are normally in contact and separate them. As a result, conduction paths established during normalization, when the detection device was exposed to a reference environment, are disrupted, and the characteristic resistance of the detection device is changed, thereby signaling the presence of the sensed substance. As noted in the reference patent, the changed resistance of the detection device is correlated to the Van der Waals' constant; and generally increases as the constant increases.

Of course, the concentration of the sensed substance to which the detection device is exposed has a bearing on the response time of the device; but given sufficient time, even extremely low concentrations of the sensed substance will be noticeably sensed. Upon return of the detection device to the reference environment, the layer of adsorbate gradually dissipates, returning the adsorbent particles to their normal conductive contact, and thus returning the device to its characteristic, normalized resistance.

Through extensive experimental it was discovered that the detection device disclosed in the referenced patent, while able to detect some substances, was insensitive to others. Through further study and experimentation, it was discovered that the detection device, when used in accordance with the teachings disclosed therein, was generally sensitive to those substances having a Van der Waals' constant which was greater than about 9, such as gasoline or diesel fuel, for example. However, its lack of sensitivity to certain other substances presented severe limitations on the usefulness of the detection device, inasmuch as a host of common substances have a Van der Waals' constant of about 9 or less. Thus, detection of carbon dioxide, carbon monoxide, propane, acetylene, natural gas and the like, all of which have a Van der Waals' constant of 9 or less, was impossible when using the detection device as taught in the Dolan et al patent.

Many years of research effort were spent attempting to modify the prior art detection device so that it would be able to detect such substances. If it were able to detect carbon dioxide and carbon monoxide it could be fabricated as a component in a fire detector and thus be useful to save both life and property. If it were able to detect natural gas, for example, it could be fabricated as a leak detector for such equipment as natural gas pipelines or LNG (liquid natural gas) transport ships. Of course, many other applications for a workable detection device able to sense substances having a Van der Waals' constant of less than 9 are readily apparent to those skilled in the art, and the uses mentioned are only by way of example.

In an effort to improve the prior art detection device and to make it sensitive to substances having a Van der Waals' constant of 9 or less, a multitude of approaches were tried. Varying the adsorbent particle size, composition, and mixture did not work. Selection of different material from which to fabricate the base member and resilient layer did not help. Changing the techniques by which the adsorbent particles were anchored to the resilient layer to thereby alter the depth and security with which each adsorbent particle was anchored also proved fruitless. Modifying the electrodes' composition and configuration was ineffectual. No matter what was tried, it was not possible to sense substances having a Van der Waals' constant of less than about 9.

However, through a fortuitous accident when the current-carrying capabilities of the prior art detection device were being measured it was noticed than an anomaly occurred at certain current and voltage levels. That is, as the voltage across the device was increased the current increased linearly in accordance with Ohms law until a specific value was reached. Thereafter the current remained relatively constant. Consistent with this finding, it was discovered that as the current through the detection device was increased, the voltage across the device also increased substantially in accordance with Ohm's Law until a specific value was reached. Thereafter, the voltage began to rise at a much faster rate than it would have as predicted by Ohm's Law.

Fortunately, while the device was being operated in this non-linear condition, (i.e., small changes in voltage across the device failed to bring substantially the changes in current through the device as predicted by Ohm's Law and very small changes in current through the device caused relatively large changes in voltage across the device) the device was tested to determine if it was still able to sense substances. Surprisingly, the new apparatus was able to detect not only those substances having a Van der Waals' constant of greater than about 9, but it was even able to detect those substances having a Van der Waals' constant of about 9 or less. A variety of liquids, vapors and gases were tested, and even helium, with a Van der Waals' constant of only 0.03412, was readily detectable. In each case, upon exposure to these substances, an easily detectable current change through the detection device occurred that was superimposed on the milliampere order of base current flowing therethrough when the device was powered by a constat voltage source, and an easily detectable voltage change across the device occurred when the device was powered by a constant current source.

The discovery that the prior art detection device, when operated in this non-linear condition, was sensitive to even those substances having a Van der Waals' constant of about 9 or less was doubly surprising since one of the prime benefits of the prior art device was that it was a "cold" sensor. That is, because it operated at the ambient temperature and employed no hot elements, it could be safely used to detect even explosive or flammable substances. Its cold operation was the result of the fact that its resistance changed upon exposure to the sensed substance and thus only a few microamperes were needed to detect this resistance change.

Operating the detection device in a non-linear manner was not an intuitive step to take for two reasons. First, non-linear operation is unnecessary when sensing substances by detecting resistance changes in the manner taught by the Dolan et al patent. Secondly, it would be thought that a high current level through the device might raise the temperature of the device to a dangerously hot level or cause ionization of the device which would render it inoperative.

Although it is not certain of the exact explanation as to the operation of his non-linear sensing apparatus, it is theorized that when an electrical current of sufficient quantity is caused to pass through the conductive, absorbent particles, the particles are heated to a temperature just slightly above the temperature of the environment to which the sensing apparatus is exposed. Then when the current saturated detection device is exposed to a substance with a Van der Waals' constant of about 9 or less, the sensed substance is adsorbed on the adsorbent particles and the heat of adsorbtion thereby released slightly raises the temperature of the particles still further so that a readily detected current change through or voltage change across the device occurs. However, it should be noted that due to its unusual property of operating in a non-linear manner at a mere milliampere order of base current, the detection device is still being operated as a "cold" type sensor, for such a minute current flow causes no substantial heating of the detection device as a whole.

It should be noted that there has been a change in the system of computing the Van der Waals' constant since the Dolan et al patent has issued, as is reflected in the current edition of the *Handbook of Chemistry and Physics*, published by the Chemical Rubber Company of Cleveland, Ohio. The current system is being used herein.

Non-linear devices such as zener diodes are employed in a variety of applications such as for voltage regulation. These devices are "current saturation" devices; that is, the current through the devices rises linearly with the voltage across the device to a certain point. As the current is increased further, the voltage remains relatively constant.

It is often desirable to regulate the current to an electronic device, but this can only be accomplished by relatively complex and expensive circuits or devices. Current regulation would be greatly simplified by a single device in which the current through the device remained relatively constant as the voltage across the device increased beyond a certain point. However, no device having this characteristic is known to exist.

SUMMARY OF THE INVENTION

It is an object of the invention to provide a sensing device capable of detecting substances having a Van der Waals' constant of either above or below 9.

It is another object of the invention to provide a sensing device which is extremely sensitive in detecting substances.

It is still another object of the invention to provide a current regulating device which operates in a non-linear manner so that as the voltage across the device is increased beyond a predetermined value the current through the device remains relatively constant.

These and other objects of the invention are accomplished by connecting a sensing device fabricated in accordance with the teachings of U.S. Pat. No. 3,045,198 in series with a current source of sufficient magnitude to place the sensor in its non-linear region. The voltage across the sensor is then measured. As the sensor is exposed to a substance having an arbitrary Van der Waals' constant, the voltage across the device varies thereby indicating the presence of the substance. The voltage measuring device may be connected to an alarm to provide a visual or aural indication of the presence of the detected substance. To maximize the sensitivity of the device when sensing relatively low concentrations of substances or to reduce the temperature effects on the detection device, the detection device may be installed in a four terminal bridge-type network.

The non-linear characteristics of the device may also be employed for simply and inexpensively regulating the current applied to a power consuming device in much the same manner that a zener diode regulates the voltage applied to a power consuming device.

BRIEF DESCRIPTION OF THE DRAWINGS

FIG. 3 is a schematic of the detection device employed to limit the current through a power consuming device;

FIG. 4 is a simplified schematic diagram of the present invention utilizing a series type circuit; and FIG. 5 is a tabulation of results obtained utilizing the form of the present invention shown in FIG. 1.

DETAILED DESCRIPTION OF THE PREFERRED EMBODIMENTS

Preliminarily, as an aid to an understanding of the present invention, it is pointed out that the basic idea involves two important concepts. The first concept is that in order for the prior art detection device of U.S. Pat. No. 3,045,198 to be sensitive to those substances having a Van der Waals' constant of about 9 or less, it must be operated in a non-linear condition. That is, very small changes in current through the device cause a relatively large change in voltage across the device, and changes in voltage across the detection device do not produce an appreciable change in the current flowing through the device that would otherwise be predicted by Ohm's Law. Thus, all aspects of the present invention require voltage or current supply means operable to bias the detection device in its non-linear region either directly or through a circuit such as a resistance network. A great number of possible circuits and arrangements of components which will fulfill this requirement will readily occur to those skilled in the art, and it should be repeated that the arrangements shown in the Figures are by merely way of non-limiting example. Of course, an exhaustive survey of all substances having Van der Waals' constant of about 9 or less has not been made to ensure the present invention's sensitivity to all of them, but a great many such substances, including those shown in the table illustrated in FIG. 5, are detectable by the sensing apparatus and method of the present invention. In addition, it should be noted that when operated in accordance with the teachings of the present invention, the detection device of U.S. Pat. No. 3,045,198 continues to be sensitive to substance having a Van der Waals' constant of greater than 9. Similarly, the present invention is sensitive to the liquid, vaporous and gaseous phases of the substances to which it is sensitive.

The second important concept involves the operating principle inherent in the present invention, which seems to be that when the detection device is driven by a current source into its non-linear region and then exposed to the sensed substance, its electrical properties change, and it is this change which form the basis by which the presence of the sensed substance may be indicated.

Thus, the present invention includes any electrical arrangement by which the changes, induced by the sensed substance, in the electrical properties of a detection device driven by a current source are used as the basis for triggering other components to indicate the presence of the sensed substance. Again, a multitude of arrangements utilizing the changing electrical properties will readily occur to those skilled in the art and the simple bridge and series circuits illustrated in FIGS. 1, 2 and 4 are merely by way of illustrative, non-limiting example.

Figure 1:
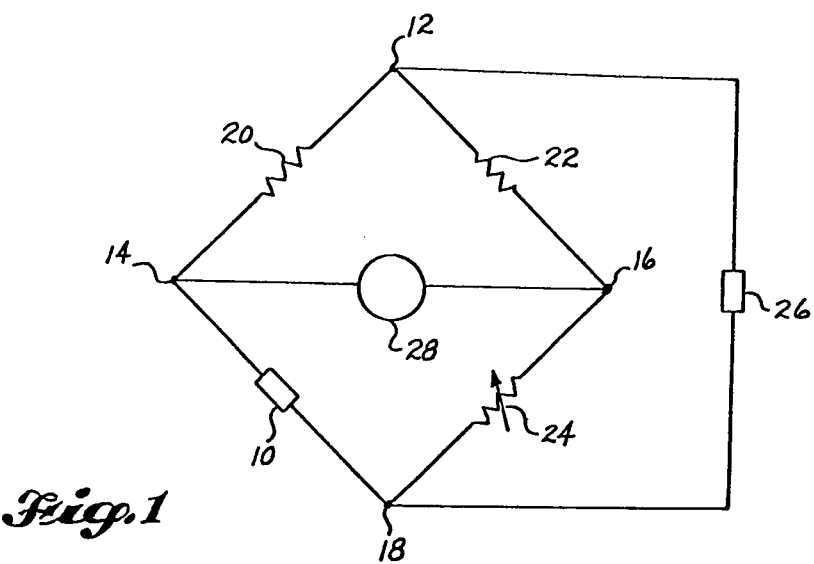
FIG. 1 is a simplified schematic diagram of the present invention utilizing a bridge type circuit.
Figure 2:
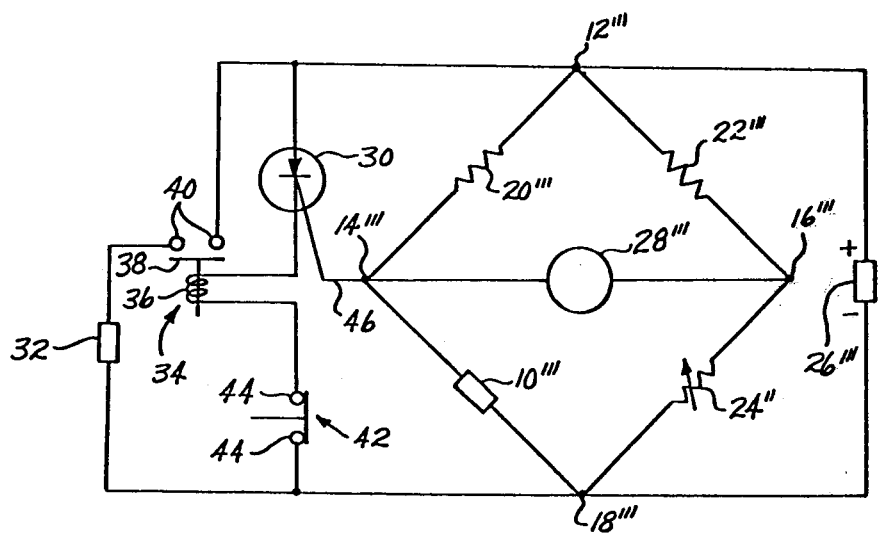
FIG. 2 is a schematic diagram of a simple alarm circuit which may be utilized with the bridge circuit shown in FIG. 1.

FIG. 1 illustrates the sensing apparatus of the present invention as comprising a detection device installed in a bridge circuit and operating in a non-linear region. The bridge circuit is of conventional design and includes a network having first, second, third and fourth terminals 12, 14, 16 and 18, respectively. A first known resistance 20 is connected across terminals 12, 14; a second known resistance 22 is connected across terminals 12, 16; and a variable resistance 24 is connected across terminals 16, 18. Although only resistance 24 is shown to be variable, it is to be understood that any or all of the known resistances 20, 22, 24 could be made variable. A detection device 10, constructed in accordance with the disclosures contained in U.S. Pat. No. 3,045,198, is connected across terminals 14, 18.

By way of non-limiting example, the detection device 10 comprises an essentially nonconducting base or body in the form of a standard cylindrical one-half watt resistor having a resistance of above 10 million ohms and having a conducting lead at each end. The body of the resistor is then coated with a thin layer of adhesive, such as adhesive type 3145 RTV manufactured by Dow Corning Company. While the adhesive is still tacky, a layer of conductive carbon particles, such as No. 2 powdered flake manufactured by the Joseph Dixon Crucible Co. of Jersey City, N.J., is applied to the body and anchored thereto by the adhesive layer. The detection device 10 is completed by establishing a conductive path between the device's terminals and the conductive particles by means of applying silver paint therebetween. When tested with a standard ohmmeter, the detection device 10 was found to have a resistance of about 900 ohms. It will be understood, however, that the resistances of the devices will vary depending upon such factors as particle composition and body configuration.

In order to determine at what current the detection device 10 enters the non-linear region, the device 10 is placed in a simple series circuit, such as illustrated in FIG. 4, comprising the device 10", a conventional variable D.C. current source 26" and a conventional voltmeter 28". As the current through the detection device 10" is increased, corresponding increases in voltage across the device 10" are observed. The voltage across the device is initially a linear function of the applied current. Beyond a certain value, however, the voltage increases at a faster rate than the current. In one operational embodiment small changes in current through the device produced corresponding voltage changes across the device 10 which were greater than predicted by Ohm's Law at about 9.5 ma. Of course, the current range at which any particular detection device 10 enters the non-linear region will vary according to the particular construction of the device 10 used.

Referring again now to FIG. 1, a current source 26 generates a predetermined current between terminals 12, 18 thereby biasing the detection device 10 into its non-linear region. Voltage indicating means 28 are then connected across terminals 14, 16. The indicating means may comprise any of a variety of equipment which are responsive to the voltage between terminals 12, 16, including a circuit for sounding an aural, visual or other alarm to signal the presence of the sensed substance. Such a circuit is shown by way of non-limiting example in FIG. 2.

Referring now to FIG. 2, we see that it includes a bridge circuit similar to that shown in FIG. 1, with those corresponding elements which are the same as those in FIG. 1 identified by a triple prime in FIG. 2. Element 30 is an SCR (Silicon Controlled Rectifier), element 32 is a Sonalert audio-type alarm No. SC628 manufactured by the P. R. Mallory Co. of Indianapolis, Ind., and element 34 is a 600 ohm relay having an actuating coil 36, contractor 38 and output terminals 40. Element 42 is a normally closed reset switch having terminals 44. In use, the bridge portion of the circuit shown in FIG. 2 is operated exactly as the bridge circuit shown in FIG. 1 with the current source 26''' supplying a predetermined current between terminals 12''', 18''' which is sufficient to cause the detection device 10''' to operate in the non-linear region. Variable resistor 24''' is adjusted to balance the bridge circuit while the detection device 10''' is exposed to a reference environment, such as room 10''' is exposed to a reference environment, such as room air.

Upon exposure of the detection device 10''' to a substance to which it is sensitive, such as carbon dioxide, its electrical properties change, generally reflected by a decrease in the flow of current therethrough or an increase in the voltage thereacross. This causes an unbalance of the bridge circuit which is sensed by the SCR through lead 46, causing the SCR to become conductive and supply current to the actuating coil 36 of the relay 34 causing contactor 38 to close across terminals 40. This supplies power to the audio alarm 32 to signal the presence of the sensed substance. The alarm is silenced by opening switch 42 which cuts off power to the actuating coil 36 of the relay 34, causing the contactor 38 to open, thereby interrupting the supply of power to the alarm 32. Opening of the switch 44 also causes the SCR 30 to cease conducting and upon removal of the detection device 10''' from the presence of the sensed substance for a period of time sufficient to allow the sensed substance to dissipate therefrom, the switch 44 may be closed again without reactivation of the alarm 32, thereby resetting the circuit shown in FIG. 1 for use again.

Returning now to FIG. 1, in operation the sensing apparatus is first exposed to a reference environment, such as pure atmospheric air, while the detection device 10 is operating in its non-linear region. After the detection device has stabilized in the reference environment, one or more of the known resistances, and preferably variable resistor 24, are varied until the voltage across terminals 14, 16 is zero as indicated by the indicating means 28. When the detection device 10 is exposed to the substance to be sensed, its electrical properties change so that the voltage thereacross causes an imbalance of the bridge circuit. This imbalance is detected by the indicating means 28 to signal the presence of the sensed substance. Upon removal of the detection device from the presence of the sensed substance, the device 10 gradually returns to its initial condition.

Tabulated in FIG. 5 are sample test results obtained using the 900 ohm detection device 10 previously described and a voltmeter as the detection device 28.

A bridge circuit is preferred for its relatively great sensitivity and ability to detect the electrical changes occurring in the current saturated detection device 10 when it is exposed to the sensed substance, as reflected by the voltage and/or current imbalances caused in the balanced bridge circuit thereby. Also, the bridge circuit allows the indicating device 28''' to be made insensitive to temperature induced variations in the property of the detection device. For example a detection device may be coated with an impervious coating and substituted for either the variable resistance 24'' or the variable resistance 20. The coated detection device would be insensitive to substances to which it was exposed, but it would respond to temperature variations in the same manner as the detection device 10.

Referring now to FIG. 4, the circuit shown therein comprises a power supply 26'' generating a constant current through the detection device 10''. The magnitude of the current through the device is sufficient to place the device in a non-linear region. In other words, as the current through the device increases from zero, the voltage across the device increases accordingly in a substantially linear manner. When the non-linear region is entered, however, the voltage change for a given current change increases greatly. The voltage across the detection device 10 is measured by a voltmeter 28'' which detects voltage variations across the detection device when the detection device 10'' is exposed to the sensed substance. Upon removal of the detection device 10'' from the presence of the sensed substance, the detection device gradually returns to its initial condition.

The operation of the circuit shown in FIG. 4 is as follows: First, the range at which the detection device 10'' enters the non-linear region is determined as has been described in reference to detection device 10. Next, the current supply 26'' is selected to provide sufficient power to the device 10'' to cause it to operate in a non-linear condition, and the device 10'' is exposed to a reference environment such as room air and allowed to normalize. Then, when the device 10'' is exposed to the sensed substance its electrical properties change. This change is reflected by a change in voltage across the device 10'' which is sensed by the voltage indicating means 28'' to signal the presence of the sensed substance. Upon return of the device 10'' to the reference environment, the device soon returns to its initial condition.

It is well recognized that a perfect current source does not exist. That is, all current sources have a less-than-infinite output impedence. Consequently, a change in voltage across the device 10'' also results in a current change through the device 10'' since the change in voltage across the output impedance of the current source produces a change in current through the output impedance. This, of course, does not depart from the basis of the invention which is that the detection device can be biased into a non-linear region by a current source and that in this non-linear region the operating conditions or electrical properties of the device change when the device is exposed to a substance having a Van der Waals' constant either above or below 9.

The surprisingly non-linear characteristics of the device allow it to be readily adapted as a current regulator since the current through the device is relatively insensitive to variations in the voltage across the device when it is biased in its non-linear region. For example, the device 10' may be placed in series with a power consuming apparatus, shown schematically as 26' in FIG. 3, which is adapted to receive a specific current. The device 10' will then insure that the current supplied to the apparatus 26' by the power supply, shown schematically as 28', is relatively constant as either the output voltage of the power supply 28' or the impedance of the apparatus 26' varies. The device may thus be operated as a current regulator in a manner analogous to the operation of a zener diode as a voltage regulator.

I claim:

1. A sensing apparatus for liquid, vaporous and gaseous substances, comprising:
   a detection device of the type having a plurality of independently anchored, electrically conductive particles which are adsorbently sensitive to liquids, vapors or gases, said particles being arranged in sequential contact to form one or more conductive paths between separated points;
   current source means electrically connected to the detection device and supplying a substantially constant current through the detection device having a magnitude sufficient to cause said detection device to operate in a non-linear region; and
   indicating means electrically connecting to the detection device to indicate when an electrical property of said detection device changes responsive to said detection device being exposed to the substance being sensed.

2. The sensing apparatus of claim 1, wherein the indicating means further includes alarm means to indicate the presence of the sensed substance.

3. The sensing apparatus of claim 1 further including a four-terminal bridge network having a first known resistance connected between the first and second terminals, a second known resistance connected between the first and third terminals and a third known resistance connected between the third and fourth terminals, at least one of the resistances being variable, and wherein said detection device is connected between the second and fourth terminals, said current source means are connected between the first and fourth terminals and the indicating means are connected between the second and third terminals.

4. The sensing apparatus according to claim 3, wherein the indicating means detect the voltage changes across the second and third terminals.

5. The sensing apparatus of claim 3 wherein a detection device having a coating impervious to said substances is substituted for one of said known resistances to minimize the temperature sensitivity of said apparatus.

6. The sensing apparatus of claim 1, wherein the detection device and the current source means are electrically connected in series, and wherein said indicating means are connected in parallel across the detection device to detect the voltage across the detection device responsive to the presence of the second substance.

7. A method of sensing liquid, vaporous and gaseous substances, comprising:
   providing a detection device of the type having a plurality of independently anchored, electrically conductive particles which are adsorbently sensitive to liquids, vapors or gases, said particles being arranged in sequential contact to form one or more conductive paths between separated points;
   biasing said detection device into a non-linear region by causing a relatively constant current to flow through said detection device; and
   detecting a change in the electrical properties of said device responsive to said detection device being exposed to the substance being sensed.

8. The method of claim 7, further comprising:
   forming a four terminal electrical network by connecting a first known resistance between the first and second terminals, connecting a second known resistance between the first and third terminals, connecting a third known resistance between the third and fourth terminals, at least one of the resistances being variable, connecting the indicating means between the second and third terminals, and connecting said detection device between the second and fourth terminals;
   supplying sufficient current between the first and fourth terminals to bias the detection device to operate in its non-linear region; and
   exposing the detection device sequentially to a reference environment and to a sensed substance thereby changing an electrical property of said device.

9. The method of claim 8 wherein said indicating means senses the change in voltage between the second and third terminals when the detection device is exposed to the sensed substance.

10. A method of sensing liquid, vaporous and gaseous substances, comprising:
    providing a detection device of the type having a plurality of independently anchored, electrically conductive particles which are adsorbently sensitive to liquids, vapors or gases, said particles being arranged in sequential contact to form one or more conductive paths between separated points;
    generating a relatively constant current through said device having a magnitude sufficient to bias said device into its non-linear region;
    measuring the voltage across said device; and
    sequentially exposing the detection device to a reference environment and to a sensed substance and examining for a change in voltage across said detection device in response thereto.

11. A method of regulating current supplied to a power consuming device, comprising:
    providing a detection device of the type having a plurality of independently anchored, electrically conductive particles which are absorbently sensitive to liquids, vapors or gases, said particles being arranged in sequential contact to form one or more conductive paths between separated terminals;
    electrically connecting said power consuming device to one of said separated terminals; and
    electrically connecting power supply means between the other of said terminals and said power consuming device, said power supply means generating sufficient power to cause said detection device to operate in its non-linear region such that the current through said power consuming device is relatively constant as either the voltage at the output of said power supply means or the impedance of said power consuming device fluctuates.

12. A current regulated power consuming circuit, comprising detection device means connected in series with said power consuming circuit, said detection device means being of the type having a plurality of independently anchored electrically conductive particles which are adsorbently sensitive to liquids, vapors or gases, said particles being arranged in sequential contact to form one or more conductive paths between separated points, said series combination of said detection device means and power consuming device being connected across power supply means adapted to produce sufficient power to cause said detection device means to operate in its non-linear region.

* * * * *